United States Patent
He et al.

(10) Patent No.: US 11,970,515 B1
(45) Date of Patent: Apr. 30, 2024

(54) CRYSTAL FORM OF BRASSINOSTEROID (BR) ANALOGUE, AND PREPARATION METHOD AND USE THEREOF

(71) Applicant: CHENGDU NEWSUN CROP SCIENCE CO., LTD., Sichuan (CN)

(72) Inventors: Qiming He, Sichuan (CN); Dan Ren, Sichuan (CN)

(73) Assignee: CHENGDU NEWSUN CROP SCIENCE CO., LTD., Sichuan (CN)

( * ) Notice: Subject to any disclaimer, the term of this patent is extended or adjusted under 35 U.S.C. 154(b) by 0 days.

(21) Appl. No.: 18/547,826

(22) PCT Filed: Mar. 29, 2022

(86) PCT No.: PCT/CN2022/083659
§ 371 (c)(1),
(2) Date: Aug. 24, 2023

(87) PCT Pub. No.: WO2023/115741
PCT Pub. Date: Jun. 29, 2023

(30) Foreign Application Priority Data

Dec. 24, 2021 (CN) .......................... 202111604062.X

(51) Int. Cl.
C07J 9/00 (2006.01)
A01N 45/00 (2006.01)
A01P 21/00 (2006.01)

(52) U.S. Cl.
CPC ................ C07J 9/00 (2013.01); A01N 45/00 (2013.01); A01P 21/00 (2021.08)

(58) Field of Classification Search
CPC ............. C07J 9/00; A01N 45/00; A01P 21/00
See application file for complete search history.

(56) References Cited

FOREIGN PATENT DOCUMENTS

| CN | 103214546 A | 7/2013 |
| CN | 103282373 A | 9/2013 |

(Continued)

OTHER PUBLICATIONS

The State Intellectual Property Office of People's Republic of China, First Office Action, Application No. 202111604062.X dated Jun. 8, 2022, in 11 pages.

(Continued)

*Primary Examiner* — Trevor Love
(74) *Attorney, Agent, or Firm* — PROCOPIO, CORY, HARGREAVES & SAVITCH LLP

(57) ABSTRACT

The present disclosure provides a novel brassinosteroid (BR) analogue, a novel crystal form, and a preparation method and use thereof. The BR analogue has a chemical formula of $C_{27}H_{46}O_7$, a chemical name of (20R,22R)-2β,3β,14α-14,20,22,25-hexahydroxy-5β,8α,9α-cholestan-6-one, and a structural formula of:

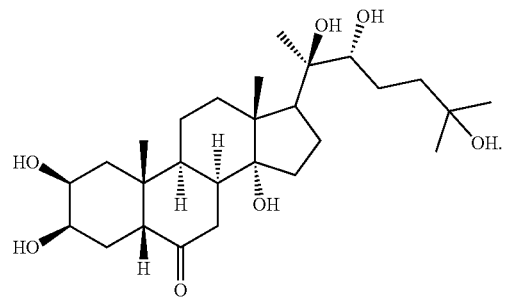

In the present disclosure, a novel crystal form with a high bioactivity is obtained by improving a recrystallization process of a naturally extracted BR analogue. This novel crystal form can be applied in the field of agriculture to promote the growth of plants.

4 Claims, 9 Drawing Sheets

(56) References Cited

FOREIGN PATENT DOCUMENTS

| CN | 109221132 | A  | 1/2019  |
|----|-----------|----|---------|
| CN | 110839645 | A  | 2/2020  |
| CN | 114276400 | A  | 4/2022  |
| RU | 2434877   | C1 | 11/2011 |

OTHER PUBLICATIONS

The State Intellectual Property Office of People's Republic of China, Second Office Action, Application No. 202111604062.X dated Aug. 10, 2022, in 12 pages.
The State Intellectual Property Office of People's Republic of China, Notification to Grant Patent Right for Invention, Application No. 202111604062.X dated Mar. 27, 2023, in 4 pages.
Thussagunpanit, et al., "Comparative Effects of Brassinosteroid and Brassinosteroid Mimic on Improving Photosynthesis, Lipid Peroxidation, and Rice Seed Set under Heat Stress," J Plant Growth Regul, dated Dec. 19, 2014, in 12 pages.
Odinokov, et al., "7,8-Dihydro Analogs of Ecdysteroids", Institute of Petroleum Chemistry and Catalysis and Zelinskii Institute of Organic Chemistry, dated Aug. 2, 2006, in 9 pages.
Patent Cooperation Treaty, International Search Report, Application No. PCT/CN2022/083659, dated Mar. 29, 2022, in 4 pages.
Suksamrarn, et al., "Stereoselective catalytic hydrogenation of /\, 7-6-ketosteroids in the presence of sodium nitrite", Tetrahedron, dated Mar. 27, 2002, in 5 pages.

CRYSTAL FORM OF BRASSINOSTEROID (BR) ANALOGUE, AND PREPARATION METHOD AND USE THEREOF

CROSS REFERENCE TO RELATED APPLICATION

This patent application is a national stage application of International Patent Application No. PCT/CN2022/083659, filed on Mar. 29, 2022, which claims the benefit and priority of Chinese Patent Application No. 202111604062.X, filed with the China National Intellectual Property Administration on Dec. 24, 2021, the disclosure of which is incorporated by reference herein in its entirety as part of the present application.

TECHNICAL FIELD

The present disclosure relates to the technical field of agrochemicals, in particular to a novel Brassinosteroid (BR) analogue, a novel crystal form, and a preparation method and use thereof.

BACKGROUND

In the 1930s, researchers at the United States Department of Agriculture (USDA) discovered that plant pollen extracts can promote plant growth. American scientist Mitchell first proposed the concept of brassins in 1970. This unknown component derived from rapeseed pollen extract is effective in promoting stem elongation and cell division in plants at extremely low concentrations. Subsequently, scientist Grove extracted a compound with brassin activity from the rapeseed pollen in 1979, determined its chemical structural formula through X-ray single crystal diffraction analysis, and named it brassinolide (BL). Brassinosteroids (BRs) have a variety of unique physiological activities that regulate plant growth. Compared with known plant growth regulators such as auxin, cytokinin, gibberellin, abscisic acid, and ethylene, the BRs show stronger bioactivity, lower dosage, and higher safety, and are available in the agriculture with a better effect of increasing production and income.

Natural BR is a general term for a class of lactone compounds and their sterol analogues. In addition to the identified BLs, more than 60 different natural structures have been discovered, collectively referred to as BRs. With a history of more than 20 years of research on natural BRs, a series of preparation processes have been developed for extracting the natural BRs from natural raw materials. Natural BR analogues (BR1 to BR6) with different structures were isolated in the patent 201210026285.7 "Use of Natural BL Analogues". Based on this, a novel natural BR analogue structure is discovered through constant in-depth development and continuous research in the present disclosure.

Compound polymorphism means that the active ingredient of a drug can form two or more molecular assembly modes during crystallization. The emergence of polymorphism is a result of kinetic competition between crystallization thermodynamics and molecular recognition. During the crystallization, changes in crystallization conditions, such as solvent composition, temperature, concentration, supersaturation, pH value, stirring speed, and impurities, may lead to changes in the configuration and conformation of particle elements inside a crystal. Alternatively, changes of the combination mode and force between each other can make the crystal show different unit cell parameters and space groups, thus forming the polymorphism. Generally speaking, a compound may have multiple crystal forms, but not all prepared crystal forms have bioactivity, such that it is extremely important to screen the dominant crystal form. In the present disclosure, based on the patent 201210026285.7 "Use of Natural BL Analogues", two kinds of new crystals are obtained by different recrystallization methods for a pollen crude extract, and have significant bioactivity.

In view of this, the present application is specifically proposed.

SUMMARY

The present disclosure provides a novel BR analogue, a novel crystal form, and a preparation method and use thereof. In the present disclosure, a BR analogue with a significantly improved bioactivity and a novel crystal form thereof can be obtained by improving and optimizing recrystallization conditions of an extracted natural BR analogue.

The present disclosure is implemented by means of the following technical solution:

The present disclosure provides a Brassinosteroid (BR) analogue, where the BR analogue has a chemical formula of $C_{27}H_{46}O_7$, a chemical name of (20R,22R)-2β,3β,14α-14,20,22,25-hexahydroxy-5β,8α,9α-cholestan-6-one, and a structural formula of:

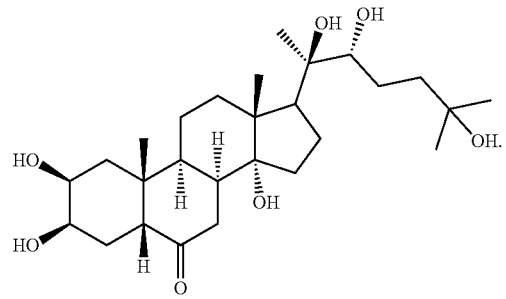

The BR analogue has the following carbon NMR data: $^{13}C$ NMR (100 MHz, C5D5N): δ 212.07, 83.72, 77.36, 76.68, 70.27, 69.37, 67.18, 51.45, 50.05, 49.44, 47.79, 43.42, 42.39, 41.55, 41.41, 40.14, 39.46, 34.16, 31.46, 29.89, 29.76, 27.48, 27.29, 21.35, 20.93, 18.96, 18.84.

The present disclosure further provides a novel crystal form of the BR analogue, where the novel crystal form is selected from the group consisting of a crystal form I and a crystal form II;

an X-ray powder diffraction (XRPD) spectrogram represented by Cu-Kα radiation and a 2θ±0.2° diffraction angle of the crystal form I shows characteristic diffraction peaks at 6.25°, 8.75°, 9.53°, 12.46°, 13.93°, 16.26°, 17.21°, 17.73°, 18.69°, 19.81°, 20.68°, 22.75°, 24.13°, 24.99°, 25.77°, 27.07°, 29.66°, 30.78°, 31.82°, 33.11°, 36.14°, 37.69°, 38.90°, 40.37°, 42.53°, and 48.76°; and an XRPD spectrogram represented by the Cu-Kα radiation and the 2θ±0.2° diffraction angle of the crystal form II shows characteristic diffraction peaks at 6.59°, 10.74°, 11.94°, 14.62°, 15.31°, 17.56°, 18.42°, 18.80°, 19.75°, 20.76°, 21.88°, 22.57°, 23.87°, 24.81°, 26.45°, 28.09°, 28.71°, 29.65°, 31.39°, 33.46°, 34.40°, 36.83°, 38.11°, 38.72°, 39.76°, 41.66°, 43.05°, 46.42°, 47.02°, and 47.45°.

Further, an infrared spectrum of the crystal form I shows characteristic peaks at wave numbers of 3,425.78 cm$^{-1}$, 2,961.01 cm$^{-1}$, 2,926.81 cm$^{-1}$, 1,696.67 cm$^{-1}$, 1,633.37 cm$^{-1}$, 1,383.39 cm$^{-1}$, 1,064.12 cm$^{-1}$, 950.79 cm$^{-1}$, and 524.36 cm$^{-1}$.

Further, an infrared spectrum of the crystal form II shows characteristic peaks at wave numbers of 3,431.58 cm$^{-1}$, 2,966.56 cm$^{-1}$, 2,931.38 cm$^{-1}$, 2,361.83 cm$^{-1}$, 1,708.24 cm$^{-1}$, 1,634.57 cm$^{-1}$, 1,455.83 cm$^{-1}$, 1,383.93 cm$^{-1}$, 1,068.20 cm$^{-1}$, and 550.62 cm$^{-1}$.

The present disclosure further provides a preparation method of the novel crystal form of the BR analogue, where a preparation process of the crystal form I includes the following steps: 1) extracting a crude extract of a natural BR analogue from rapeseed pollen; 2) dissolving 10 parts to 20 parts of the crude extract of the natural BR analogue in 20 to 30 times a methanol reagent by mass, heating at 50° C. to 80° C. to promote complete dissolution, filtering an obtained solution I into a test tube while the solution I is hot, sealing the test tube with a parafilm, piercing holes in the parafilm, cooling, and allowing the solution I to stand to conduct volatilization, to obtain a precipitated bulk white crystal I, namely the novel crystal form I of the BR analogue;

a preparation process of the crystal form II includes the following steps: 1) extracting the crude extract of the natural BR analogue from the rapeseed pollen; 2) dissolving 10 parts to 20 parts of the crude extract of the natural BR analogue in 75 to 85 times a toluene reagent, heating at 50° C. to 80° C. to promote complete dissolution, filtering an obtained solution II into a test tube while the solution II is hot, sealing the test tube with a parafilm, piercing holes in the parafilm, cooling, and allowing the solution II to stand to conduct volatilization, to obtain a precipitated granular white crystal, namely the novel crystal form II of the BR analogue.

The present disclosure provides a preparation method of a novel crystal form of a BR analogue. A preparation process of a crude extract is the same as that in the patent 201210026285.7 "Use of Natural BL Analogues", including the following steps: 1) extracting crushed rapeseed pollen with 80% to 100% (V/V) of an ethanol aqueous solution, conducting solid-liquid separation, retaining a resulting filtrate (optionally further concentrating the filtrate) to obtain an alcohol-soluble extract; 2) mixing the alcohol-soluble extract with 0% to 60% (V/V) of an ethanol aqueous solution, extracting with ethyl acetate, retaining a resulting ethyl acetate layer and adding esterase to allow an incomplete reaction, and drying to obtain an ester-soluble extract; and 3) loading the ester-soluble extract on a silica gel chromatographic column, conducting elution with a mixture of methanol and ethyl acetate, collecting an obtained eluate containing a natural BR analogue, and drying to obtain a crude extract of the natural BR analogue.

The present disclosure further provides use of the BR analogue or the novel crystal form thereof in the field of agriculture, where the BR analogue or the novel crystal form thereof is used for promoting plant growth.

Compared with the prior art, the present disclosure has the following advantages and beneficial effects:

1. In examples of the present disclosure, the BR analogue and the crystal form thereof have a significant bioactivity.
2. In examples of the present disclosure, the preparation method of the novel crystal form of the BR analogue improves a method for purifying a pollen crude extract. Two novel crystal forms with a high bioactivity are obtained through recrystallization, and can be applied in the field of agriculture to promote the growth of plants.

BRIEF DESCRIPTION OF THE DRAWINGS

In order to describe technical solutions of implementations of the present disclosure more clearly, accompanying drawings required for the embodiments are briefly described below. Apparently, the following accompanying drawings show merely some embodiments of the present disclosure, and therefore should not be regarded as the limitations to the scope. Those of ordinary skill in the art may further derive other relevant accompanying drawings from these accompanying drawings without creative efforts.

DETAILED DESCRIPTION OF THE EMBODIMENTS

Figure 1:
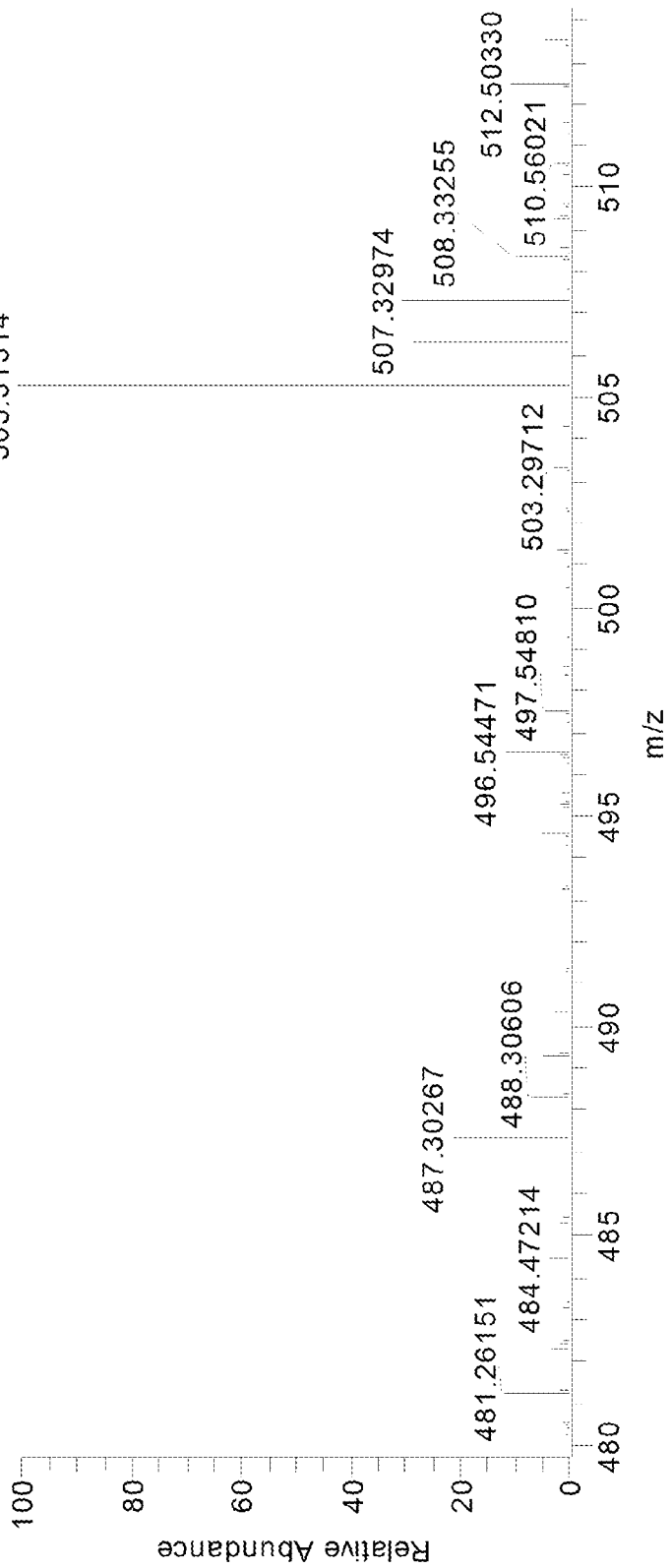
FIG. 1 shows a high-resolution mass spectrum of the BR analogue provided in an example of the present disclosure.

In order to make the objectives, technical solutions and advantages of the present disclosure clearer, the present disclosure will be further described in detail below in combination with the embodiments and the accompanying drawings. The schematic implementations of the present disclosure and descriptions of the schematic implementations are merely intended to explain the present disclosure and are not intended to limit the present disclosure.

In the following descriptions, numerous particular details are set forth in order to provide a thorough understanding of the present disclosure. However, it is obvious for a person of ordinary skill in the art that it is not necessary to adopt these specific details to implement the present disclosure. In other examples, in order to avoid confusing the present disclosure, well-known circuits, software, methods, or the like are not described in detail.

Reference throughout this specification to "one embodiment", "an embodiment", "one example" or "an example" means that a particular feature, structure, or characteristic described in connection with the embodiment or example is included in at least one embodiment of the present disclosure. Thus, the appearances of the phrases "one embodiment", "an embodiment", "one example" or "an example" in various places throughout this specification are not necessarily all referring to the same embodiment or example. Furthermore, the particular features, structures, or characteristics may be combined in any suitable combination and/or sub-combination in one or more embodiments or examples. In addition, it should be understood by the person of ordinary skill in the art that the drawings provided herein are illustrative only but are unnecessarily drawn according to a proportion. As used herein, the term "and/or" includes any and all combinations of one or more related items listed.

Example 1

This example provided a preparation method of a novel crystal form I of a BR analogue, including the following steps:

1. An Extraction Method of a Crude Extract of a Natural BR Analogue
   1) crushed rapeseed pollen was extracted with 80% to 100% (V/V) of an ethanol aqueous solution, solid-liquid separation was conducted, a resulting filtrate (optionally the filtrate was further concentrated) was retained to obtain an alcohol-soluble extract;
   2) the alcohol-soluble extract was mixed with 0% to 60% (V/V) of an ethanol aqueous solution, extracted with ethyl acetate, a resulting ethyl acetate layer was retained and esterase was added to allow an incomplete reaction, and dried to obtain an ester-soluble extract; and
   3) the ester-soluble extract was loaded on a silica gel chromatographic column, elution was conducted with a mixture of methanol and ethyl acetate, an obtained eluate containing a natural BR analogue was collected, and dried to obtain a crude extract of the natural BR analogue.

2. Recrystallization of the Novel Crystal Form I of the BR Analogue 10 g of the crude extract of the natural BR analogue extracted in step 1 was dissolved in 20 to 30 times a methanol reagent by mass, heated at 50° C. to 80° C. to promote complete dissolution, an obtained solution I was filtered into a test tube while the solution I was hot, the test tube was sealed with a parafilm, holes were pierced in the parafilm, cooled, and the solution I was allowed to stand to conduct volatilization for about 5 d, to obtain a precipitated bulk white crystal I, namely the novel crystal form I of the BR analogue.

This example provided a preparation method of a novel crystal form II of the BR analogue, including the following steps:

1. An Extraction Method of a Crude Extract of a Natural BR Analogue
   1) crushed rapeseed pollen was extracted with 80% to 100% (V/V) of an ethanol aqueous solution, solid-liquid separation was conducted, a resulting filtrate (optionally the filtrate was further concentrated) was retained to obtain an alcohol-soluble extract;
   2) the alcohol-soluble extract was mixed with 0% to 60% (V/V) of an ethanol aqueous solution, extracted with ethyl acetate, a resulting ethyl acetate layer was retained and esterase was added to allow an incomplete reaction, and dried to obtain an ester-soluble extract; and
   3) the ester-soluble extract was loaded on a silica gel chromatographic column, elution was conducted with a mixture of methanol and ethyl acetate, an obtained eluate containing a natural BR analogue was collected, and dried to obtain a crude extract of the natural BR analogue.

2. Recrystallization of the Novel Crystal Form II of the BR Analogue 10 g of the crude extract of the natural BR analogue extracted in step 1 was dissolved in 75 to 85 times a toluene reagent, heated at 50° C. to 80° C. to promote complete dissolution, an obtained solution II was filtered into a test tube while the solution II was hot, the test tube was sealed with a parafilm, holes were pierced in the parafilm, cooled, and the solution II was allowed to stand to conduct volatilization for about 10 d, to obtain a precipitated granular white crystal II, namely the novel crystal form II of the BR analogue.

Comparative Example 1

This comparative example differed from Example 1 in that the recrystallization method was different: 15 g of a BR analogue were dissolved in 0.5 L of a methanol solution, 1 L of an acetonitrile solvent was added and stirred evenly to obtain a mixture, the test tube was sealed with a parafilm, holes were pierced in the parafilm, cooled, and the mixture was allowed to stand to conduct volatilization for about 20 d, to obtain small crystal particles on a wall of the test tube. These particles were not suitable for X-ray testing.

Comparative Example 2

This comparative example differed from Example 1 in that the recrystallization method was different: 5 g of a BR analogue were dissolved in 0.5 L of an ethanol solution, a resulting mixture was filtered and allowed to stand to conduct volatilization for one week, the solution turned into a yellow viscous liquid without crystals.

Comparative Example 3

This comparative example differed from Example 1 in that the recrystallization method was different: 10 g of a BR analogue were dissolved in 0.3 L of a methanol solution, 0.8 L of an acetonitrile solvent was added and stirred evenly to obtain a mixture, the mixture was filtered, placed in a long test tube for slow volatilization, and no crystals were precipitated. After the solvent evaporated completely, a yellow thick liquid substance remained.

The recrystallization system and method used in Comparative Example 1 to Comparative Example 3 were different from the recrystallization method and system provided in Example 1 of the present disclosure. It was seen from the results that the crystals of the present disclosure could not be precipitated in Comparative Example 1 to Comparative Example 3.

The two kinds of white crystals obtained in Example 1 were subjected to XRD, infrared spectrum, hydrogen spectrum, and carbon spectrum detection to determine their structural formulas, and a thermal stability of the crystals was tested by TG and DSC, and the following results were obtained:

1. In the present disclosure, the BR analogue had a molecular structure with a chemical formula of $C_{27}H_{46}O_7$, a chemical name of (20R,22R)-2β,3β,14α-14,20,22,25-hexahydroxy-5β,8α,9α-cholestan-6-one, and a structural formula of:

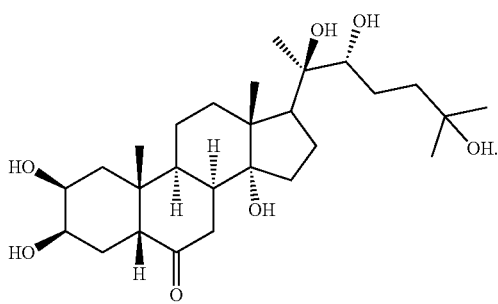

Figure 2:
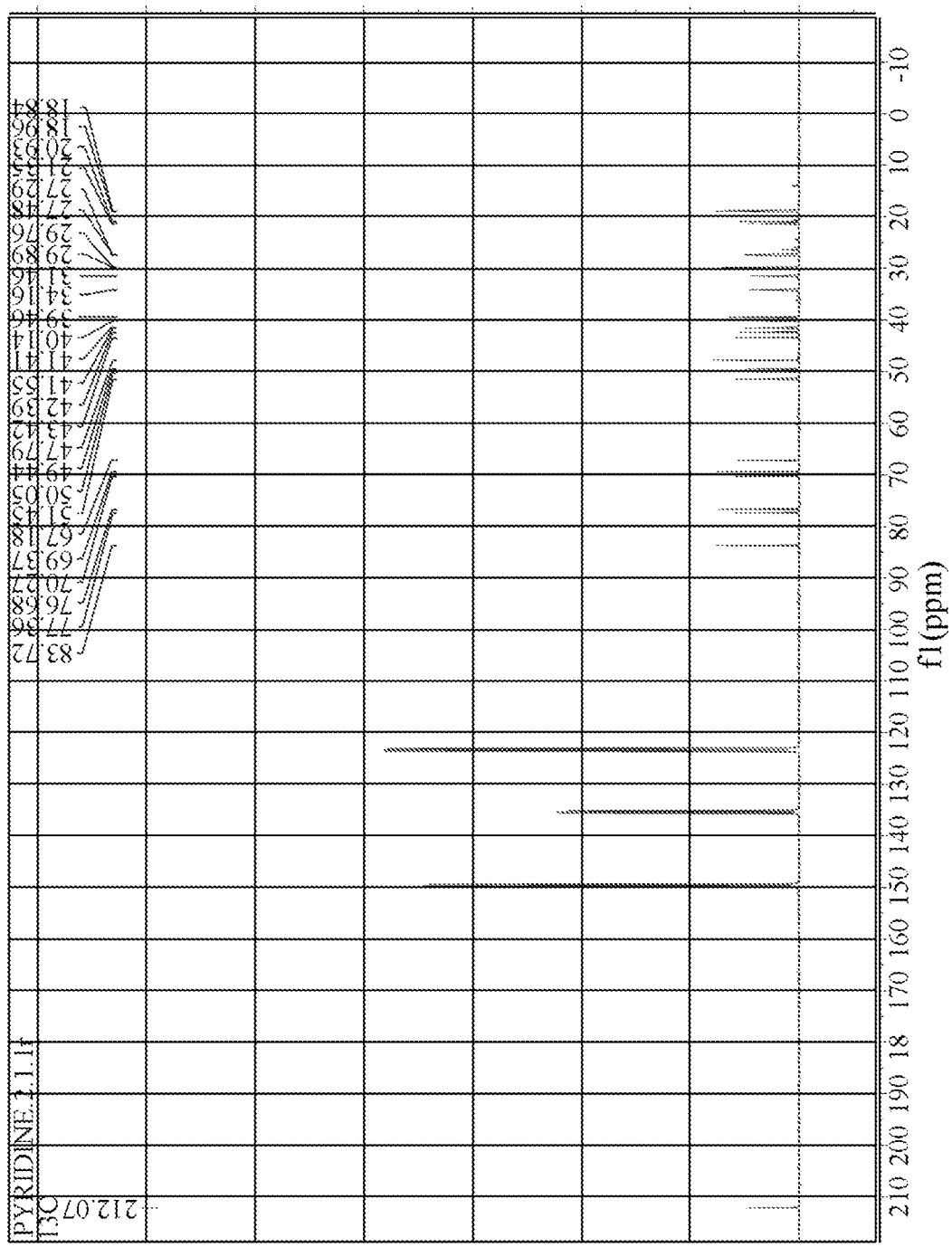
FIG. 2 shows a carbon NMR spectrum of the novel crystal form of the BR analogue provided in an example of the present disclosure.
Figure 3:
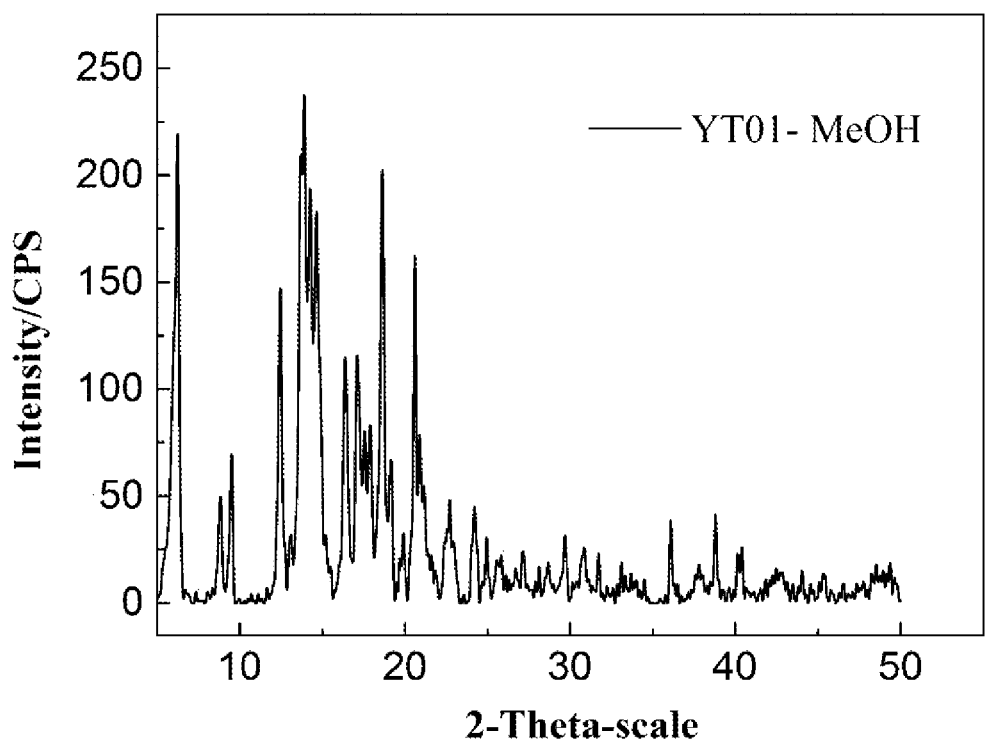
FIG. 3 shows an X-ray powder diffraction (XRPD) spectrogram of the novel crystal form I provided in an example of the present disclosure.

2. In the present disclosure, the BR analogue had a high-resolution mass spectrometry result as shown in FIG. 1, and the compound had a sodium-added molecular weight of 505.31314 and a molecular formula of $C_{27}H_{46}O_7$+Na.
3. In the present disclosure, the BR analogue had the following carbon NMR data shown in FIG. 2: $^{13}C$ NMR (100 MHz, C5D5N): δ 212.07, 83.72, 77.36, 76.68, 70.27, 69.37, 67.18, 51.45, 50.05, 49.44, 47.79, 43.42, 42.39, 41.55, 41.41, 40.14, 39.46, 34.16, 31.46, 29.89, 29.76, 27.48, 27.29, 21.35, 20.93, 18.96, 18.84.
4. In the present disclosure, XRD diffraction results of the novel crystal form I were shown in FIG. 3: an XRPD spectrogram represented by Cu-Kα radiation and a 2θ±0.2° diffraction angle of the crystal form I showed characteristic diffraction peaks at 6.25°, 8.75°, 9.53°, 12.46°, 13.93°, 16.26°, 17.21°, 17.73°, 18.69°, 19.81°, 20.68°, 22.75°, 24.13°, 24.99°, 25.77°, 27.07°, 29.66°, 30.78°, 31.82°, 33.11°, 36.14°, 37.69°, 38.90°, 40.37°, 42.53°, and 48.760.

Figure 4:
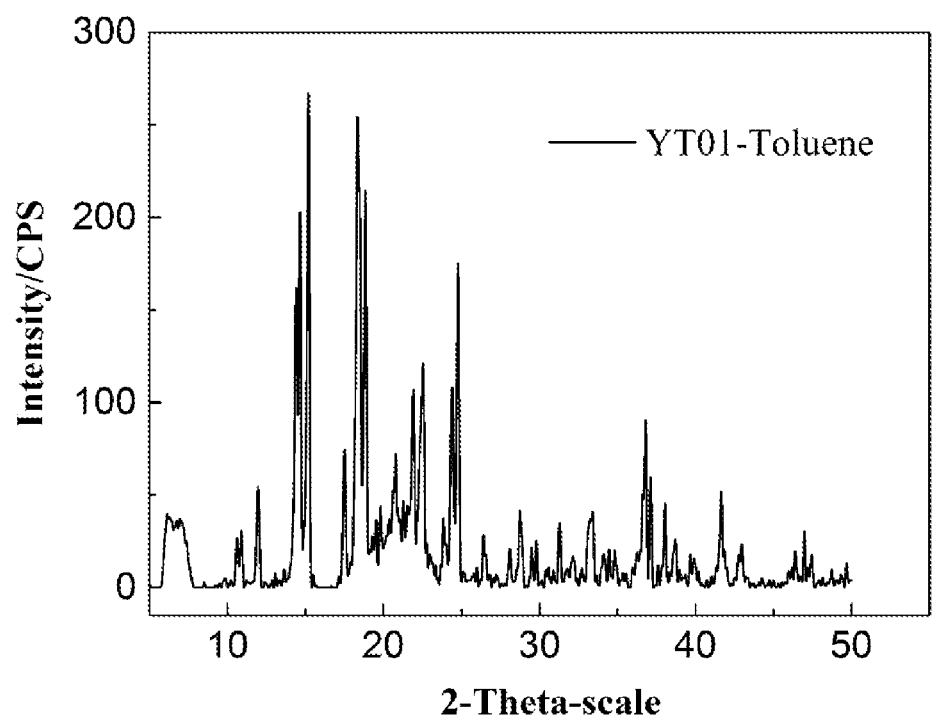
FIG. 4 shows an X-ray powder diffraction (XRPD) spectrogram of the novel crystal form II provided in an example of the present disclosure.
Figure 5:
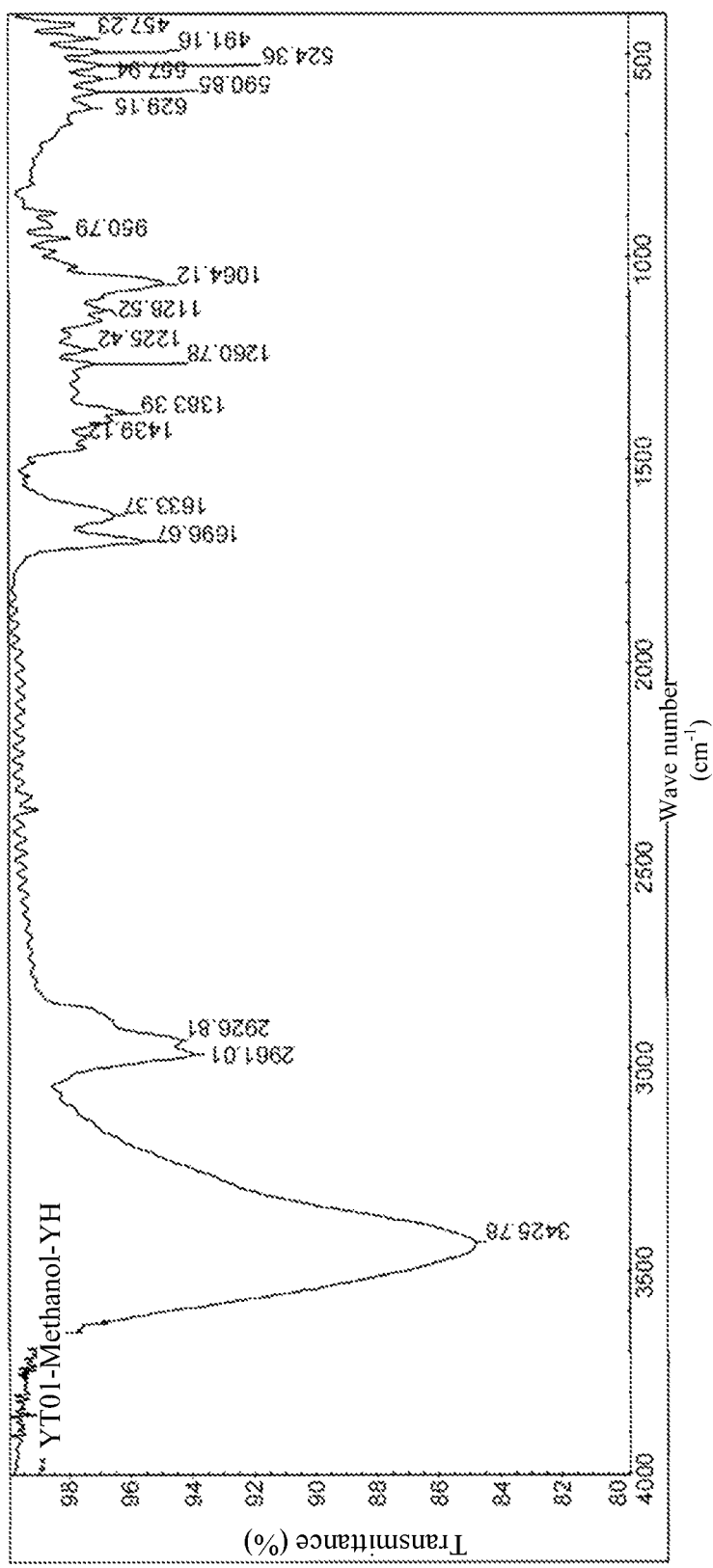
FIG. 5 shows an infrared spectrogram of the novel crystal form I provided in an example of the present disclosure.

In the present disclosure, XRD diffraction results of the novel crystal form II were shown in FIG. 4: an XRPD spectrogram represented by the Cu-Kα radiation and the 2θ±0.2° diffraction angle of the crystal form II shows characteristic diffraction peaks at 6.59°, 10.74°, 11.94°, 14.62°, 15.31°, 17.56°, 18.42°, 18.80°, 19.75°, 20.76°, 21.88°, 22.57°, 23.87°, 24.81°, 26.45°, 28.09°, 28.71°, 29.65°, 31.39°, 33.46°, 34.40°, 36.83°, 38.11°, 38.72°, 39.76°, 41.66°, 43.05°, 46.42°, 47.02°, and 47.45°.
5. In the present disclosure, the results of the infrared spectrum of the novel crystal form I were shown in FIG. 5. An infrared spectrum of the crystal form I shows characteristic peaks at wave numbers of 3,425.78 $cm^{-1}$, 2,961.01 $cm^{-1}$, 2,926.81 $cm^{-1}$, 1,696.67 $cm^{-1}$, 1,633.37 $cm^{-1}$, 1,383.39 $cm^{-1}$, 1,064.12 $cm^{-1}$, 950.79 $cm^{-1}$, and 524.36 $cm^{-1}$.

Figure 6:
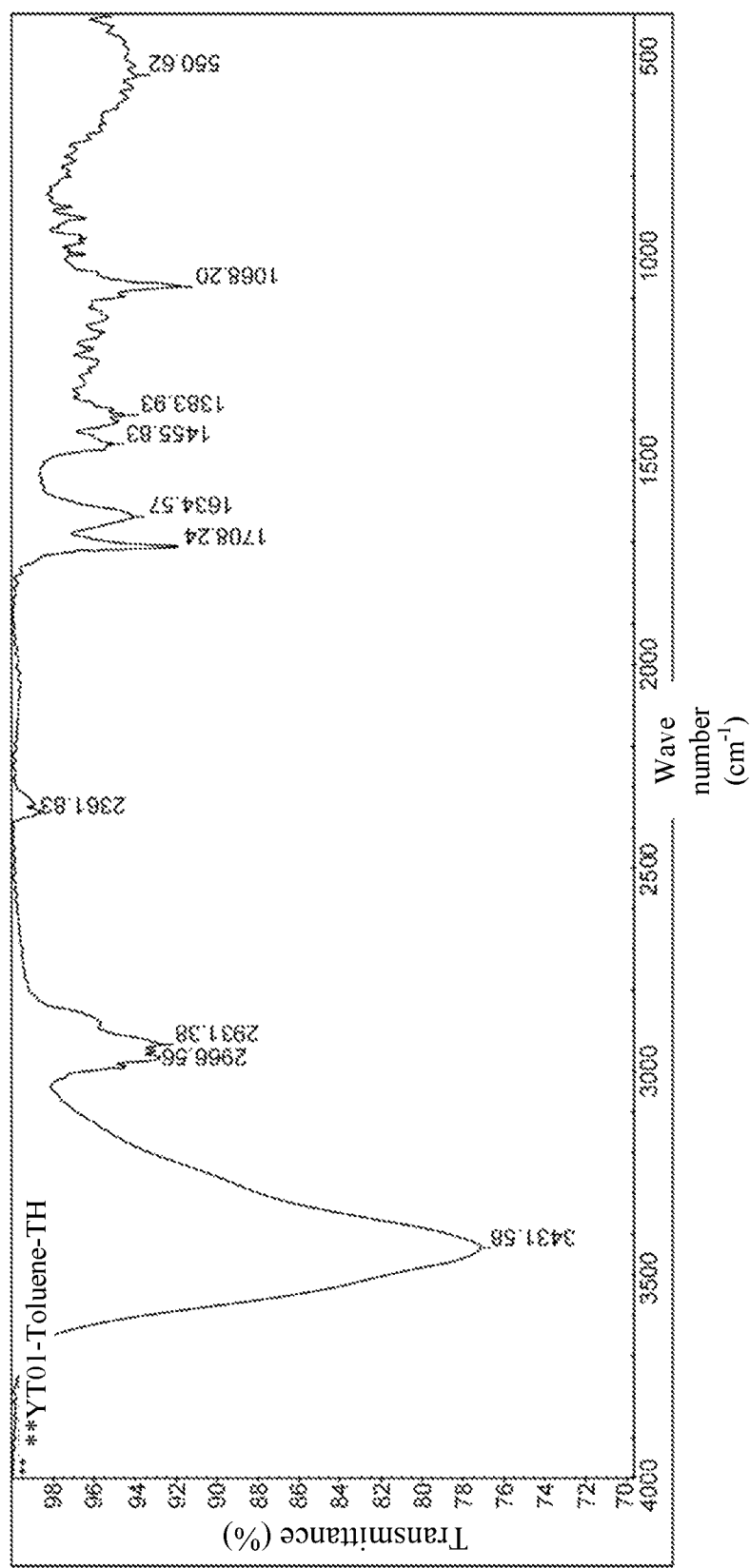
FIG. 6 shows an infrared spectrogram of the novel crystal form II provided in an example of the present disclosure.

In the present disclosure, the results of the infrared spectrum of the novel crystal form II were shown in FIG. 6. An infrared spectrum of the crystal form II shows characteristic peaks at wave numbers of 3,431.58 $cm^{-1}$, 2,966.56 $cm^{-1}$, 2,931.38 $cm^{-1}$, 2,361.83 $cm^{-1}$, 1,708.24 $cm^{-1}$, 1,634.57 $cm^{-1}$, 1,455.83 $cm^{-1}$, 1,383.93 $cm^{-1}$, 1,068.20 $cm^{-1}$, and 550.62 $cm^{-1}$.

Figure 7:
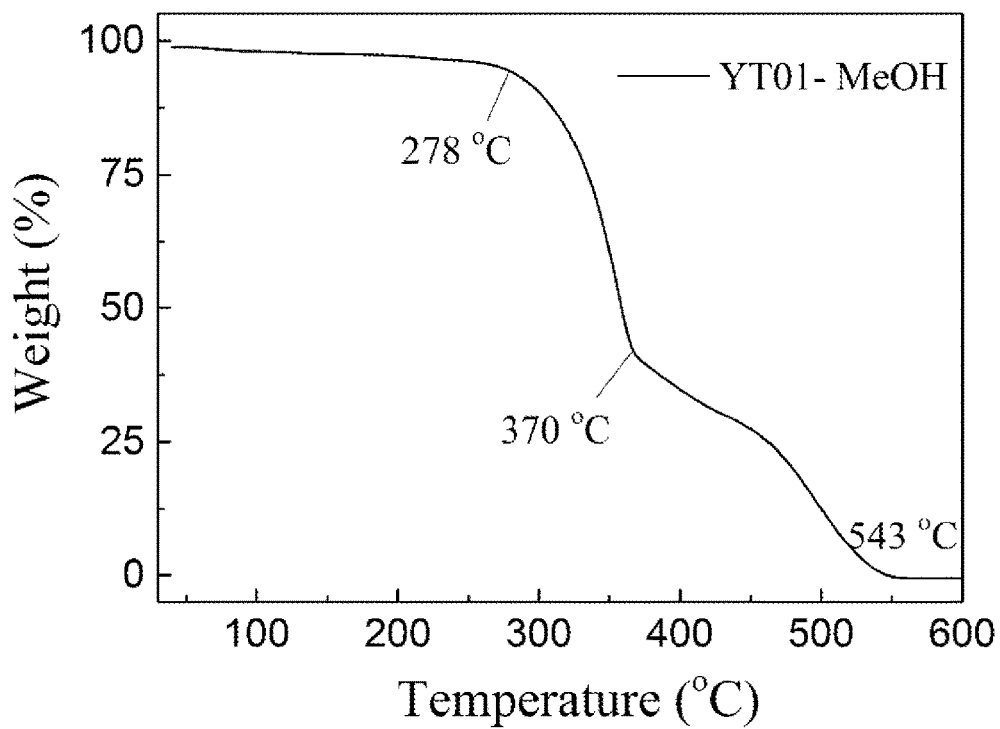
FIG. 7 shows a thermogravimetric (TG) curve of the novel crystal form I provided in an example of the present disclosure.

6. In the present disclosure, the TG results of the novel crystal form I were shown in FIG. 7, and the TG curve showed that the compound of the present disclosure had desirable stability from room temperature to 280° C.

Figure 8:
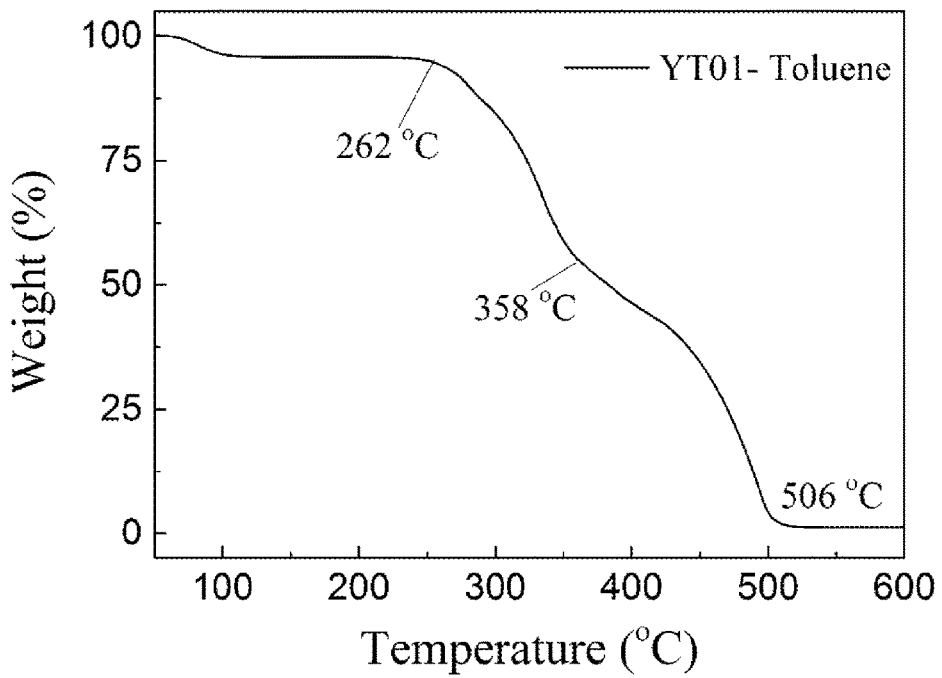
FIG. 8 shows a TG curve of the novel crystal form II provided in an example of the present disclosure.
Figure 9:
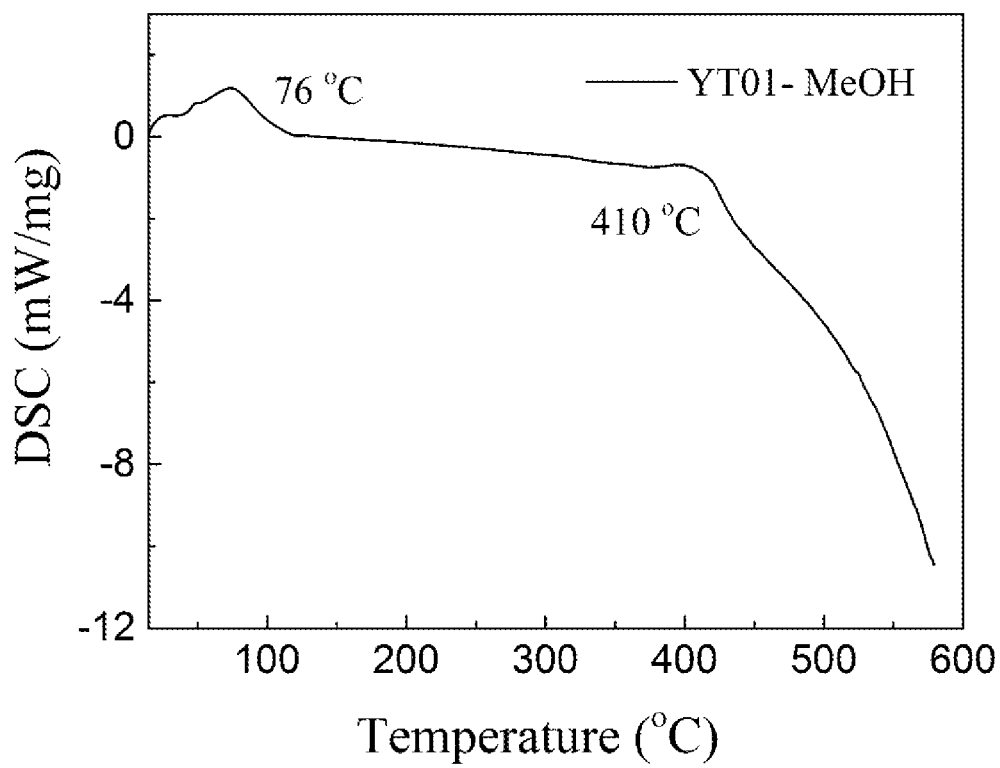
FIG. 9 shows a differential scanning calorimetry (DSC) image of the novel crystal form I provided in an example of the present disclosure.

In the present disclosure, the TG results of the novel crystal form II were shown in FIG. 8, and the TG curve showed that the compound of the present disclosure had desirable stability from room temperature to 260° C.
7. In the present disclosure, the DSC results of the novel crystal form I were shown in FIG. 9. There were two exothermic peaks with physical interference in the spectrum, with peak positions at 76° C. and 410° C., respectively.

Figure 10:
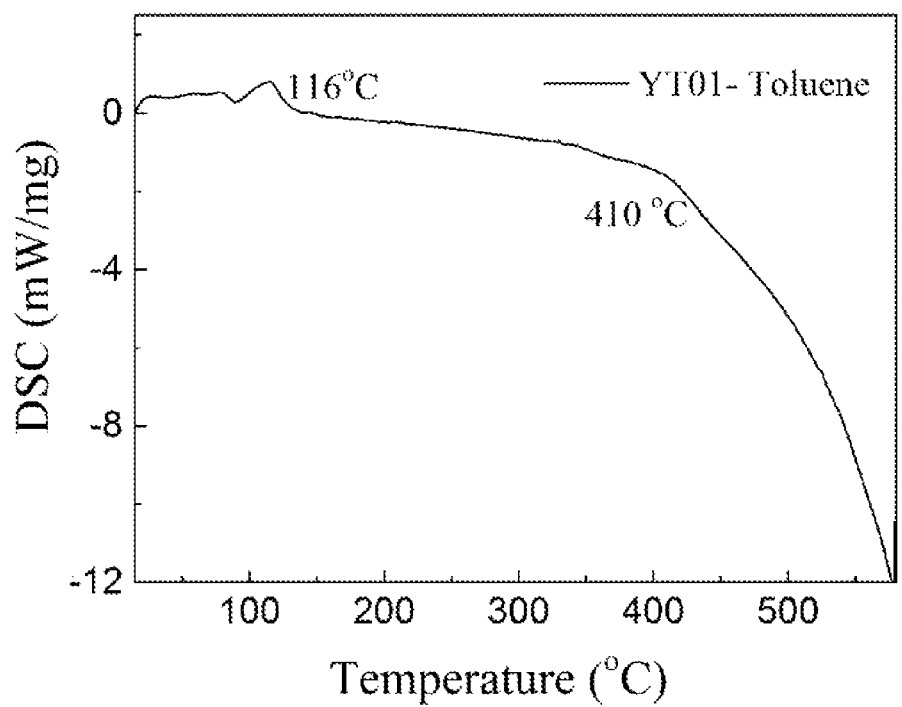
FIG. 10 shows a DSC image of the novel crystal form II provided in an example of the present disclosure.

In the present disclosure, the DSC results of the novel crystal form II were shown in FIG. 10. There were two exothermic peaks with physical interference in the spectrum, with peak positions at 116° C. and 410° C., respectively.

Example 2

Research on the stability and solubility of the novel crystal form provided in Example 1 of the present disclosure
1. Stability Research Appropriate amounts of the crystal form I and crystal form II were separately placed in a high-temperature environment at 80° C.±2° C. for stability experiments, and the experimental results were shown in Table 1. It was seen from the results that the crystal form was highly stable in the high-temperature environment, and no crystal form change occurred.

TABLE 1

Stability test results of novel crystal forms in the present disclosure

| Sample No. | Test time (d) | Content (%) | Content of other substances (%) | XRPD |
|---|---|---|---|---|
| Novel crystal form I of the present disclosure | 0 | 99.98 | 0.02 | Unchanged |
| | 5 | 99.93 | 0.07 | Unchanged |
| | 10 | 99.96 | 0.04 | Unchanged |
| Novel crystal form II of the present disclosure | 0 | 99.87 | 0.13 | Unchanged |
| | 5 | 99.84 | 0.16 | Unchanged |
| | 10 | 99.87 | 0.13 | Unchanged |

Figure 11:
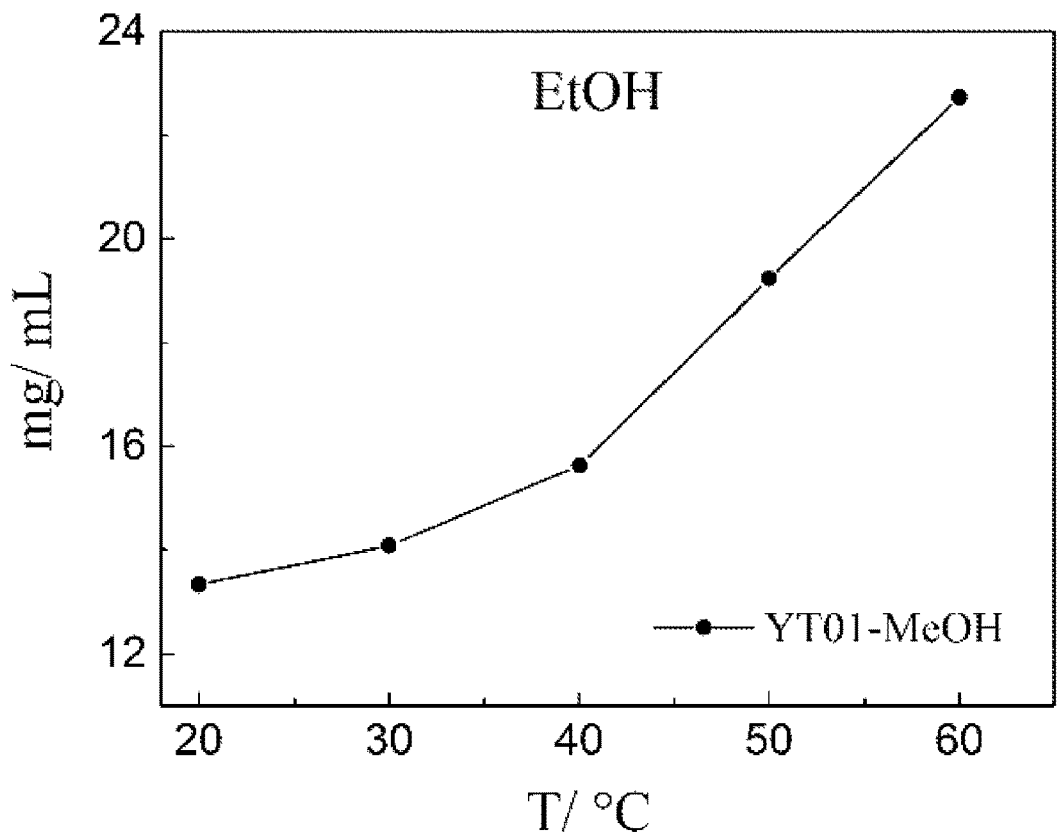
FIG. 11 shows a solubility curve in ethanol of the novel crystal form I provided in an example of the present disclosure.
Figure 12:
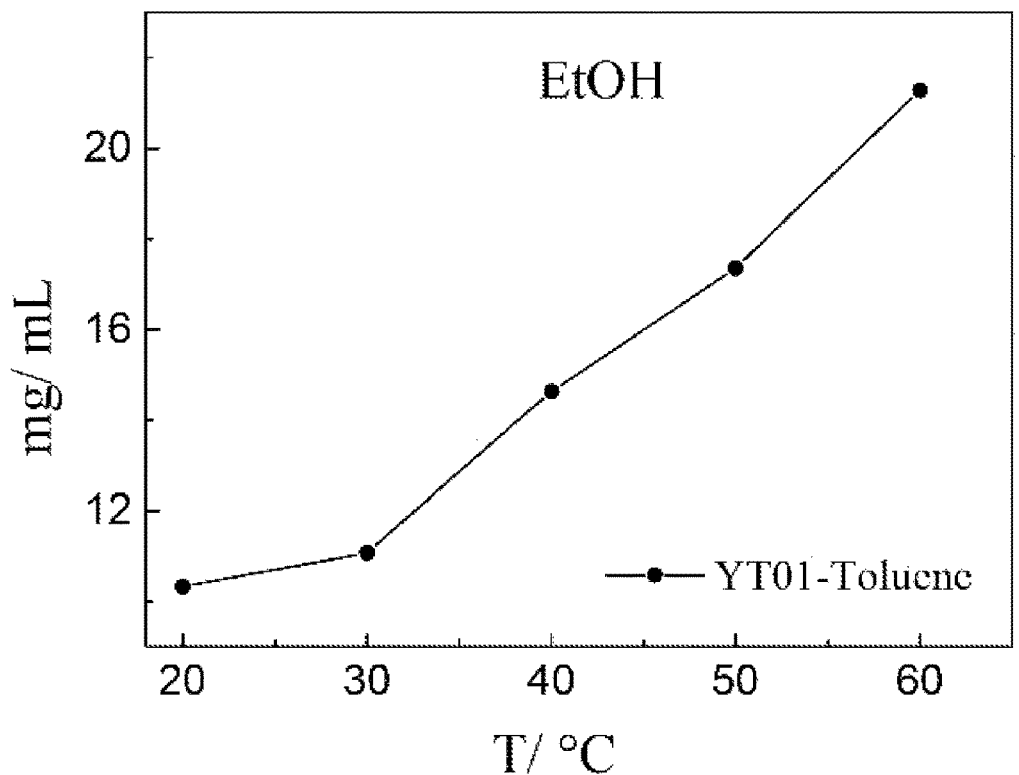
FIG. 12 shows a solubility curve in ethanol of the novel crystal form II provided in an example of the present disclosure.
Figure 13:
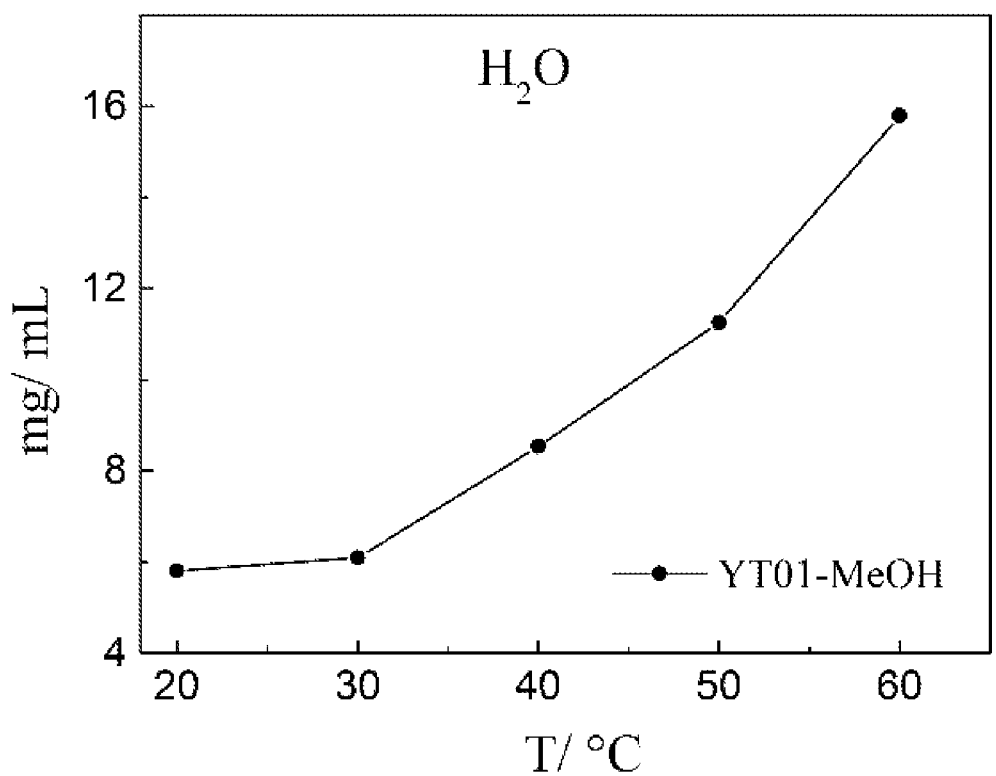
FIG. 13 shows a solubility curve in water of the novel crystal form I provided in an example of the present disclosure.
Figure 14:
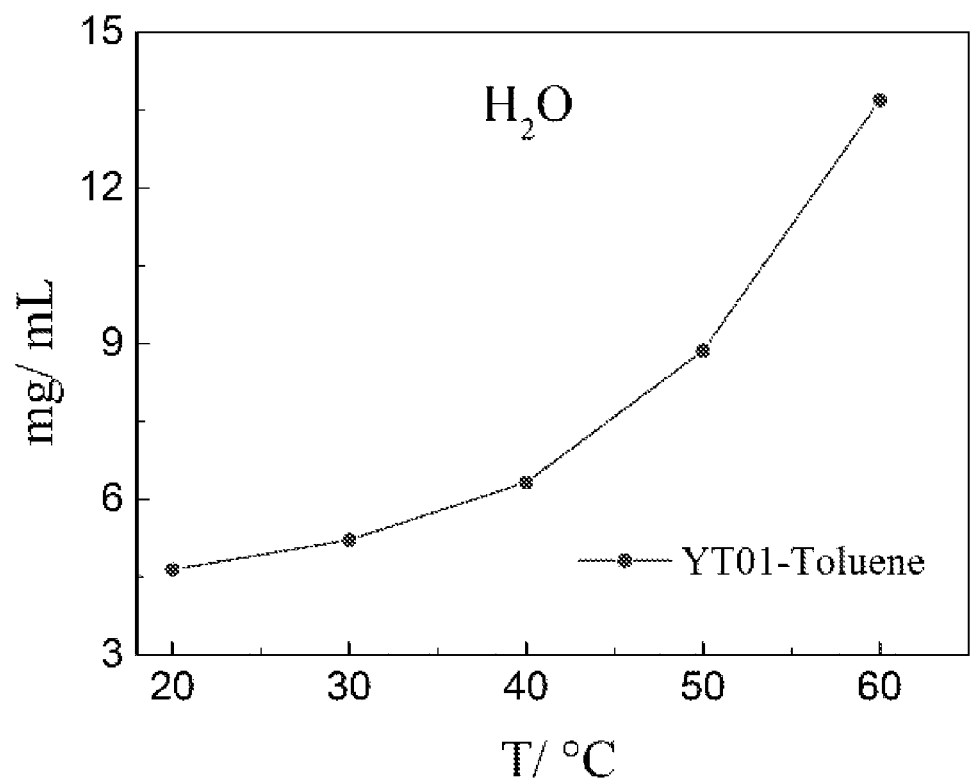
FIG. 14 shows a solubility curve in water of the novel crystal form II provided in an example of the present disclosure.

2. Solubility Research
(1) 50 mg of the crystal form I and crystal form II were separately added to a test tube, slowly added with ethanol dropwise at different temperatures while conducting vibration until completely dissolved. Weighing was conducted and a total mass was recorded, converted into volume, expressed as mg/mL. The experimental results were shown in FIG. 11 and FIG. 12.
(2) 50 mg of the crystal form I and crystal form II were separately added to a test tube, slowly added with water dropwise at different temperatures while conducting vibration until completely dissolved. Weighing was conducted and a total mass was recorded, converted into volume, expressed as mg/mL. The experimental results were shown in FIG. 13 and FIG. 14.

It was seen from the results that the crystal form I and crystal form II showed desirable solubility in both ethanol and water.

Example 3

The example of the present disclosure provided use of the novel crystal form I and the novel crystal form II in promoting plant growth, specifically an experiment of promoting growth of tobacco seedlings was taken as an example, the steps were as follows:

1. Experimental Samples:

In the present disclosure, the novel crystal form I and the novel crystal form II each were prepared with anhydrous ethanol into a 10 mg/ml mother solution, and used immediately during the experiment.

2. Experimental Design:

TABLE 2

Drug concentration design

| SN | Sample name | Drug concentration (ppm) |
|---|---|---|
| 1 | Novel crystal form I of the present disclosure | 0.003<br>0.03<br>0.3 |
| 2 | Novel crystal form II of the present disclosure | 0.003<br>0.03<br>0.3 |
| CK | Water | — |

3. Experimental Method:

Tobacco seedlings with a seedling age of 7 d were transplanted and planted in a cultivation room, and the seedlings were subjected to recovery for 2 d before testing. After the treatment agent was formulated according to the experimental design, the leaves of the tobacco seedlings were evenly sprayed, and each treatment was repeated 3 times, with 2 plants in each repetition, that is, 6 seedlings in each treatment. It was advisable to ensure that the liquid drug did not drip when spraying, so as to prevent the drug from entering the soil and affecting the experimental results. The RGB AREA_MM parameter (leaf area/mm$^2$) of the tobacco was recorded with a plant phenotype instrument before and 7 d before the administration, and a growth rate of the leaf area was calculated to evaluate a growth-promoting effect of the drug. The formula for calculating a leaf area growth rate was as follows:

Growth rate (%)=(final leaf area−initial leaf area)×100%/initial leaf area

4. Experimental Results:

The growth rate of leaf area of different treatment groups 7 d after drug treatment was shown in Table 3. It was seen from the experimental results that the new crystal forms I and II of the present disclosure both exhibited obvious growth-promoting effects at a concentration of 0.003 ppm 7 d after treatment.

TABLE 3

Determination results of tobacco growth promotion in different treatment groups

| Sample | Drug concentration (ppm) | 7-day leaf area growth rate (%) |
|---|---|---|
| Novel crystal form I of the present disclosure | 0.003<br>0.03<br>0.3 | 179.02 ± 0.15<br>166.45 ± 0.18<br>145.98 ± 0.39 |
| Novel crystal form II of the present disclosure | 0.003<br>0.03<br>0.3 | 169.02 ± 0.26<br>153.44 ± 0.19<br>150.31 ± 0.39 |
| CK | — | 112.32 ± 0.26 |

Example 4

The example of the present disclosure provided use of the novel crystal form I and the novel crystal form II in promoting plant growth, specifically an experiment of immersing corn seeds to promote germination and growth of corn was taken as an example, the steps were as follows:

1. Experimental Samples:

In the present disclosure, the novel crystal form I was prepared with anhydrous ethanol into a 10 mg/ml mother solution, and used immediately during the experiment.

2. Experimental Design:

TABLE 4

Drug concentration design

| SN | Sample name | Drug concentration (ppm) |
|---|---|---|
| 1 | Novel crystal form I of the present disclosure | 0.003<br>0.03<br>0.3 |
| CK | Water | — |

3. Experimental Method:

The agents were prepared according to the experimental design. 20 normal plump corn seeds were selected, placed in the agent, and immersed at 26° C. for 24 h. The seeds were washed with water, placed in a culture box and placed in a constant-temperature incubator for germination. The germination was conducted in 2 periods: 14 h of light illumination, at 28° C.; 10 h in the dark, at 25° C., and for 7 d. Each treatment was repeated 3 times. During the whole experiment, 5 ml of water was regularly added with a pipette at 9:00 every day to keep the culture box moist. After 7 days, the germination rate was counted, the shoot length and root length were measured, and the root vigor and shoot vigor were calculated.

Germination rate=germinated number of seeds treated on 7th day/total number of treated seeds×100%;

Bud vigor index=germination rate of 7th day×seedling bud length of 7th day;

Root vigor index=germination rate of 7th day×seedling root length of 7th day.

4. Experimental Results:

The determination results of an effect of each treatment group on the germination and growth of corn seeds were shown in Table 5. It was seen from the experimental results that the novel crystal form I of the present disclosure had a germination-promoting effect on corn at a concentration of 0.03 ppm compared with the water control. From the perspective of root and bud vigor indexes, the novel crystal form I of the present disclosure had an effect of improving the root vigor index and bud vigor index. The novel crystal form I of the present disclosure at a concentration of 0.03 ppm showed the best effect, which was obviously better than that of the control CK.

TABLE 5

Determination results of effect of different treatment groups on corn germination and growth

| Sample | Drug concentration (ppm) | Germination rate (%) | Root vigor index | Bud vigor index |
| --- | --- | --- | --- | --- |
| Novel crystal form I of the present disclosure | 0.003 | 72.12 ± 1.15 | 8.80 ± 0.29 | 7.77 ± 0.36 |
| | 0.03 | 77.34 ± 1.99 | 10.89 ± 0.24 | 10.93 ± 0.17 |
| | 0.3 | 75.38 ± 2.37 | 9.77 ± 0.53 | 9.26 ± 0.24 |
| CK | — | 66.31 ± 1.18 | 6.46 ± 0.33 | 6.27 ± 0.25 |

Example 5

The example of the present disclosure provided use of the novel crystal form II in promoting stress resistance of plants, specifically an experiment of promoting cold resistance of tobacco was taken as an example, the steps were as follows:

1. Experimental Samples:

In the present disclosure, the novel crystal form II was prepared with anhydrous ethanol into a 10 mg/ml mother solution, and used immediately during the experiment.

2. Experimental Design:

TABLE 6

Drug concentration design

| SN | Sample name | Drug concentration (ppm) |
| --- | --- | --- |
| 1 | Novel crystal form II of the present disclosure | 0.003 |
| | | 0.03 |
| | | 0.3 |
| CK | Water | — |

3. Experimental Method:

After the treatment agents were prepared according to Table 6, the leaves of the tobacco seedlings were evenly sprayed in the morning. Each treatment was repeated 3 times, with 2 plants in each repetition, that is, a total of 6 seedlings in each treatment, and it was advisable that the drug solution did not drip. After 1 d of recovery, cold injury (4° C.) treatment was conducted, while other conditions remained the same as those during normal culture. The chlorophyll fluorescence QY-max parameter (theoretical maximum photosynthetic capacity) and Fv/Fm (maximum photon yield of PSII) of tobacco were recorded before drug treatment, after 6 h and 24 h of low-temperature treatment, and after 24 h of recovery at room temperature (25° C.) separately with a plant phenotype instrument.

4. Experimental Results:

QY-max represents the theoretical maximum photosynthetic capacity of plants, and the smaller its reduction rate, the better the plant's low-temperature resistance. Fv/Fm-lss represents the maximum photon yield of PSII, similar to QY-max, the smaller its reduction rate, the better the plant's low-temperature resistance. It was seen from Table 7 that the QY-max and Fv/Fm-lss of each treatment decreased after 6 h of low-temperature treatment. The reduction rate of QY-max and Fv/Fm-lss of the novel crystal form II of the present disclosure at a concentration of 0.03 ppm was significantly lower than that of the water control. Table 8 showed a change rate of QY-max and Fv/Fm-lss among the treatments after 24 h of low-temperature treatment. It was seen that the differences among the treatments gradually decreased with the prolongation of the low-temperature time. Afterwards, each treatment was placed at room temperature (25° C.) for recovery. As shown in Table 9, it was seen that after 24 h of recovery, a recovery effect of the novel crystal form II at each concentration was better than that of the clean water control, and this effect was the best at a concentration of 0.03 ppm. In summary, the novel crystal form II of the present disclosure had bioactivity of anti-low temperature.

TABLE 7

Determination results of low-temperature treatment for 6 h

| Sample | Drug concentration (ppm) | QY-max change rate (%) | Fv/Fm-lss change rate (%) |
| --- | --- | --- | --- |
| Novel crystal form II of the present disclosure | 0.003 | −10.4 ± 0.13 | −30.1 ± 0.22 |
| | 0.03 | −3.6 ± 0.33 | −14.3 ± 0.13 |
| | 0.3 | −7.9 ± 0.25 | −26.4 ± 0.27 |
| CK | — | −15.3 ± 0.42 | −36.5 ± 0.17 |

TABLE 8

Determination results of low-temperature treatment for 24 h

| Drug Sample | concentration (ppm) | QY-max change rate (%) | Fv/Fm-lss change rate (%) |
|---|---|---|---|
| Novel crystal form II of the present disclosure | 0.003 | −31.0 ± 0.18 | −46.1 ± 0.28 |
| | 0.03 | −27.6 ± 0.16 | −33.4 ± 0.12 |
| | 0.3 | −30.0 ± 0.27 | −44.4 ± 0.25 |
| CK | — | −32.3 ± 0.12 | −50.9 ± 0.23 |

TABLE 9

Determination results of room-temperature recovery for 24 h

| Sample | Drug concentration (ppm) | QY-max change rate (%) | Fv/Fm-lss change rate (%) |
|---|---|---|---|
| Novel crystal form II of the present disclosure | 0.003 | −10.0 ± 0.24 | −16.2 ± 0.27 |
| | 0.03 | −0.6 ± 0.18 | 0.3 ± 0.16 |
| | 0.3 | −5.2 ± 0.13 | −4.5 ± 0.21 |
| CK | — | −14.2 ± 0.12 | −20.5 ± 0.22 |

The objectives, the technical solutions and the beneficial effects of the present disclosure are further described in detail by means of the above specific implementation, and it should be understood that what is described above is only the specific implementation of the present disclosure and is not intended to define the scope of protection of the present disclosure. Any modifications, equivalent substitutions, improvements, etc. within the spirit and principles of the present disclosure are intended to be encompassed within the scope of protection of the present disclosure.

What is claimed is:

1. A crystal form of a brassinosteroid (BR) analogue, wherein the BR analogue has a chemical formula of $C_{27}H_{46}O_7$, a chemical name of (20R,22R)-2β,3β,14α-14,20,22,25-hexahydroxy-5β,8α,9α-cholestan-6-one, and a structural formula of:

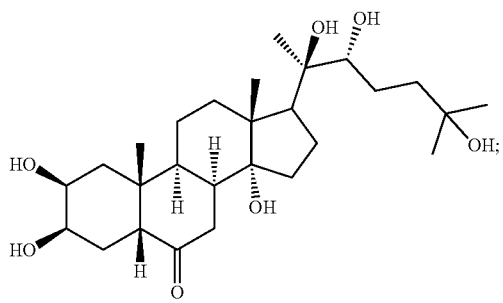

the crystal form is selected from the group consisting of a crystal form I and a crystal form II; an X-ray powder diffraction (XRPD) spectrogram represented by Cu-Kα radiation and a 2θ±0.2° diffraction angle of the crystal form I shows characteristic diffraction peaks at 6.25°, 8.75°, 9.53°, 12.46°, 13.93°, 16.26°, 17.21°, 17.73°, 18.69°, 19.81°, 20.68°, 22.75°, 24.13°, 24.99°, 25.77°, 27.070, 29.660, 30.780, 31.820, 33.110, 36.140, 37.690, 38.900, 40.370, 42.530, and 48.760; and an XRPD spectrogram represented by the Cu-Kα radiation and the 2θ±0.2° diffraction angle of the crystal form II shows characteristic diffraction peaks at 6.59°, 10.74°, 11.94°, 14.62°, 15.31°, 17.56°, 18.42°, 18.80°, 19.75°, 20.76°, 21.88°, 22.57°, 23.87°, 24.81°, 26.45°, 28.09°, 28.71°, 29.65°, 31.39°, 33.46°, 34.40°, 36.83°, 38.11°, 38.72°, 39.76°, 41.66°, 43.05°, 46.42°, 47.02°, and 47.450;

an infrared spectrum of the crystal form I shows characteristic peaks at wave numbers of 3,425.78 $cm^{-1}$, 2,961.01 $cm^{-1}$, 2,926.81 $cm^{-1}$, 1,696.67 $cm^{-1}$, 1,633.37 $cm^{-1}$, and 1,064.12 $cm^{-1}$; and an infrared spectrum of the crystal form II shows characteristic peaks at wave numbers of 3,431.58 $cm^{-1}$, 2,966.56 $cm^{-1}$, 1,708.24 $cm^{-1}$, 1,634.57 $cm^{-1}$, 1,383.93 $cm^{-1}$, and 1,068.20 $cm^{-1}$.

2. A preparation method of the crystal form of the BR analogue according to claim 1, wherein a preparation process of the crystal form I comprises the following steps: 1) extracting a crude extract of a natural Brassinosteroid (BR) analogue from rapeseed pollen; 2) dissolving 10 parts to 20 parts of the crude extract of the natural BR analogue in 20 to 30 times a methanol reagent by mass, heating to promote complete dissolution, filtering an obtained solution I into a test tube while the solution I is hot, sealing the test tube with a parafilm, piercing holes in the parafilm, cooling, and allowing the solution I to stand to conduct volatilization, to obtain a precipitated bulk white crystal I, namely the crystal form I of the BR analogue; a preparation process of the crude extract includes the following steps: 1) extracting crushed rapeseed pollen with 80% to 100% by volume concentration (V/V) of an ethanol aqueous solution, conducting solid-liquid separation, retaining a resulting filtrate (optionally further concentrating the filtrate) to obtain an alcohol-soluble extract; 2) mixing the alcohol-soluble extract with 0% to 60% (V/V) of an ethanol aqueous solution, extracting with ethyl acetate, retaining a resulting ethyl acetate layer and adding esterase to allow an incomplete reaction, and drying to obtain an ester-soluble extract; and 3) loading the ester-soluble extract on a silica gel chromatographic column, conducting elution with a mixture of methanol and ethyl acetate, collecting an obtained eluate containing a natural BR analogue, and drying to obtain a crude extract of the natural BR analogue.

3. A preparation method of the crystal form of the BR analogue according to claim 1, wherein a preparation process of the crystal form II comprises the following steps: 1) extracting the crude extract of the natural BR analogue from the rapeseed pollen; 2) dissolving 10 parts to 20 parts of the crude extract of the natural BR analogue in 75 to 85 times a toluene reagent, heating to promote complete dissolution, filtering an obtained solution II into a test tube while the solution II is hot, sealing the test tube with a parafilm, piercing holes in the parafilm, cooling, and allowing the solution II to stand to conduct volatilization, to obtain a precipitated granular white crystal, namely the crystal form II of the BR analogue; a preparation process of the crude extract includes the following steps: 1) extracting crushed rapeseed pollen with 80% to 100% by volume concentration (V/V) of an ethanol aqueous solution, conducting solid-liquid separation, retaining a resulting filtrate (optionally further concentrating the filtrate) to obtain an alcohol-soluble extract; 2) mixing the alcohol-soluble extract with 0% to 60% (V/V) of an ethanol aqueous solution, extracting with ethyl acetate, retaining a resulting ethyl acetate layer and adding esterase to allow an incomplete reaction, and drying to obtain an ester-soluble extract; and 3) loading the ester-soluble extract on a silica gel chromatographic column, conducting elution with a mixture of methanol and ethyl acetate, collecting an obtained eluate containing a natural BR analogue, and drying to obtain a crude extract of the natural BR analogue.

4. A method for promoting plant growth using the crystal form of the BR analogue according to claim 1.

* * * * *